US00PP28090P2

(12) United States Plant Patent
Hansen

(10) Patent No.: US PP28,090 P2
(45) Date of Patent: Jun. 6, 2017

(54) ***SEDUM* PLANT NAMED 'JADE TUFFET'**

(50) Latin Name: ***Sedum* hybrid**
Varietal Denomination: Jade Tuffet

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 14 days.

(21) Appl. No.: 14/756,613

(22) Filed: Sep. 24, 2015

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

Garden Center Magazine 2014 *Sedum* Sunsparkler Jade TuffetPPAF retrieved on Nov. 29, 2016, retrieved from the Internet at <http://www.gardencentermag.com/product/sunsparkler-jade-tuffet/> pp. 1-3.*

Northwest Horticulture 2014-2015 Product List, retrieved on Nov. 29, 2016, retrieved from the Internet at <http://www.northwesthort.com/media/17946/2014-2015%20product%20list-2.nov.2014%20published.pdf> pp. 1, 20, 27, 36, 44-47.*

Pluto Plant Variety Database Nov. 30, 2016 for Phedimus 'Jade Tuffet' retrieved on Dec. 1, 2016, retrieved from the Internet at <https://www.3.wipo.int/pluto/user/en/index.jsp> one page.*

The Plant List 2013 retrieved on Dec. 1, 2016, retrieved from the Internet at <http://www.theplantlistorg/tpl1.1/record/kew-2411242> 2 pp.*

* cited by examiner

*Primary Examiner* — June Hwu
(74) *Attorney, Agent, or Firm* — Penny J. Aguirre

(57) ABSTRACT

A new cultivar of *Sedum* plant named 'Jade Tuffet' characterized by its very compact and mounded plant habit reaching about 38 cm in height, its foliage that is 70% smaller and narrower than is typical with similar sized *sedum* plants, its very heavy basal branching, its foliage that emerges in spring shiny green and turns reddish green during the summer months when grown under intense sun, its very large inflorescences of medium pink flowers that appear in late summer and completely surround the mound of foliage, its bright cherry red stems, and its very high resistance to foliage blight and powdery mildew.

2 Drawing Sheets

Botanical classification: *Sedum* hybrid.
Variety denomination: 'Jade Tuffet'.

BACKGROUND OF THE INVENTION

The present invention relates to a new and distinct cultivar of *Sedum* plant, botanically of hybrid origin and known as *Sedum* 'Jade Tuffet' referred to hereinafter by its cultivar name, 'Jade Tuffet'. The new cultivar of *Sedum* is a hardy herbaceous perennial grown for use as a landscape and container plant and is particularly suitable as a groundcover.

'Jade Tuffet' arose from an ongoing breeding program by the Inventor in Hudsonville, Mich. The objective was to obtain new cultivars of *Sedums* with a compact, tight, short, well mounded and non-flapping plant habit, shiny green foliage and be disease free throughout the entire growing season requiring no fungicide sprays.

The new cultivar arose from a controlled cross made by hand-pollinating individual *sedum* flowers in August of 2010 between unnamed and unpatented plants from the Inventors breeding program as male and female parents. The Inventor selected 'Jade Tuffet' out of 900 seedlings as a single unique plant in July of 2012.

Asexual reproduction of the new cultivar was first accomplished by tip stem cuttings in May of 2012 in Hudsonville, Mich. Propagation by tip stem cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Jade Tuffet' as a unique cultivar of *Sedum*.

1. 'Jade Tuffet' exhibits a very compact and mounded plant habit reaching about 36 cm in height.
2. 'Jade Tuffet' exhibits foliage that is 70% smaller and narrower than is typical with similar sized *sedum* plants.
3. 'Jade Tuffet' exhibits very heavy basal branching with over 30 basal branches produced per winter crown.
4. 'Jade Tuffet' exhibits foliage that emerges in spring shiny green and turns reddish green during the summer months when grown under intense sun.
5. 'Jade Tuffet' exhibits very large inflorescences of medium pink flowers that appear in late summer and completely surround the mound of foliage.
6. 'Jade Tuffet' exhibits bright cherry-red stems.
7. 'Jade Tuffet' exhibits very high resistance to foliage blight and powdery mildew requiring no fungicide spraying.

The female parent differs from 'Jade Tuffet' in being shorter in height (15 cm), and in having leaves that are narrower, pale green, and glaucous, in having red stems, and flowers that are white in color. The male parent differs from 'Jade Tuffet' in being much taller in height (60 cm), in having larger leaves, in having only 8 to 10 basal branches per winter crown and in having shorter inflorescences that blooms only the top of the plant. 'Jade Tuffet' can be most closely compared to *Sedum* 'Pure Joy' (U.S. Plant Pat. No. 24,194) and 'Soft Cloud' (patent abandoned). Both are similar to 'Jade Tuffet' in having a compact and mounded plant habit and in having narrow foliage. Both differ from 'Jade Tuffet' in having foliage that is glaucous and blue-green in color and does not turn reddish under full sun conditions, in having flowers that are paler pink in color, and in being 20% shorter in height.

BRIEF DESCRIPTION OF THE DRAWINGS

The accompanying colored photographs illustrate the overall appearance and distinct characteristics of the new *Sedum*.

The photograph in FIG. 1 was taken in August of a plant about 15 months in age as grown outdoors in a 1-gallon container in Hudsonville, Mich. and provides a side view of 'Jade Tuffet' in bloom.

Figure 1:
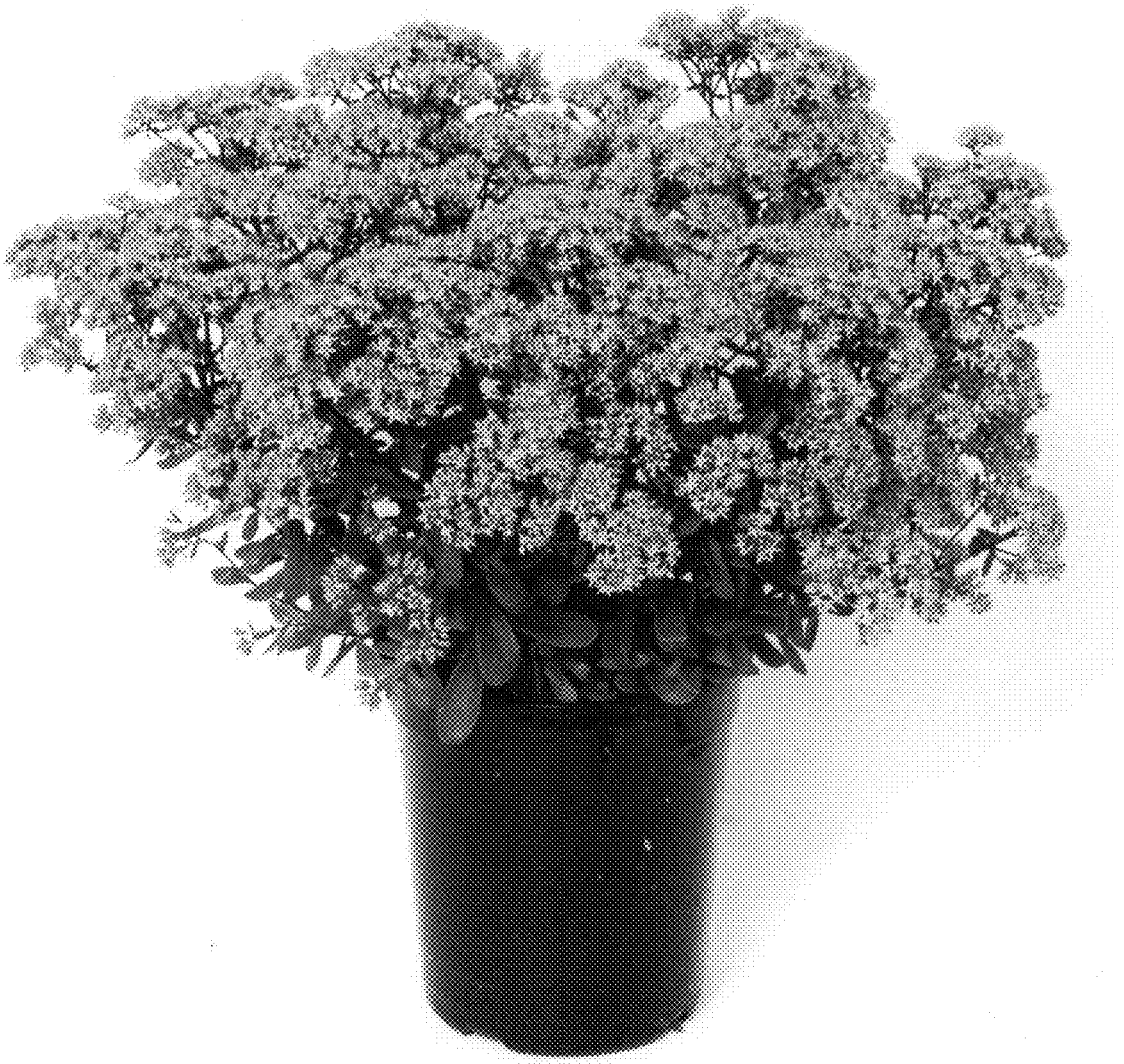
Figure 2:
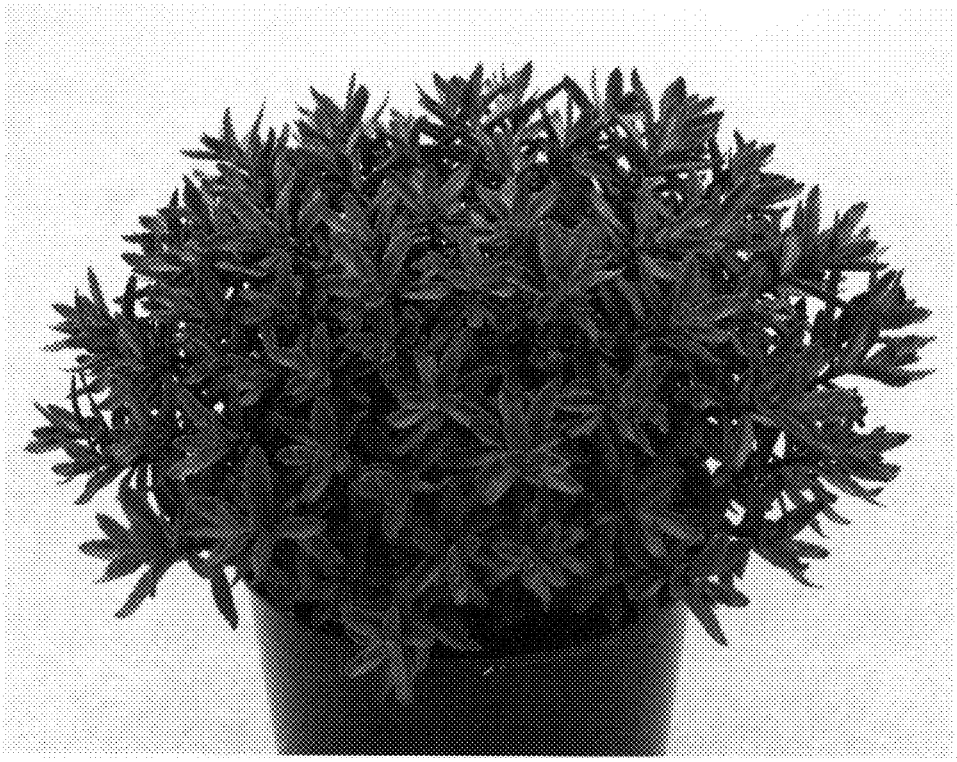

The photograph in FIG. 2 was taken in May of a plant about 15 months in age as grown outdoors in a 2-gallon container in Hudsonville, Mich. and provides a view of the spring foliage (and summer foliage if grown in shade) of 'Jade Tuffet'.

Figure 3:
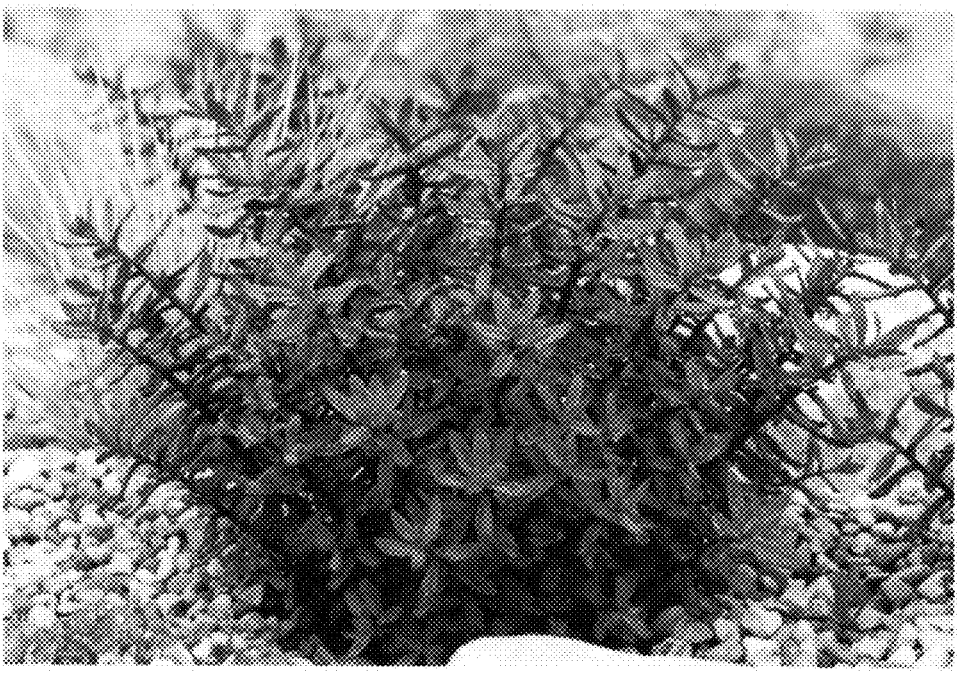

The photograph in FIG. 3 was taken in June of a plant about 9 months in age as grown in a trial garden in Hudsonville, Mich. and provides a view of the summer foliage when grown in intense sunlight.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 9 month-old plants of 'Jade Tuffet' as grown in the ground Hudsonville, Mich. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—6 weeks in mid to late summer.

*Plant type.*—Herbaceous perennial.

*Plant habit.*—Very compact, mounded, and well-branched, suitable as a mid sized *Sedum* ground-cover.

*Height and spread.*—Reaches an average of 36 cm in height and 46 cm in spread.

*Hardiness.*—At least hardy in U.S.D.A. Zones 4 to 9.

*Diseases pest.*—Highly resistant to *sedum* foliage blight (caused by *Septoria sedi*) and powdery mildew (caused by *Erysiphe cichoracearum*), no occurrence of either has been observed to date.

*Root description.*—Fibrous, 199D in color.

*Propagation.*—Tip stem cuttings.

*Root development.*—Roots initiate in 15 days and 60 days are required to produce a young plant in a 4 inch container.

*Growth rate.*—Vigorous.

Stem description:

*Stem shape.*—Oval.

*Stem size.*—An average of 40 cm in length (including terminal peduncle), and 7 mm in width with lateral branches an average of 15 cm in length and 2 mm in width.

*Internode length.*—Average of 1.5 cm.

*Stem color.*—Spring; 138B heavily suffused with 184A, mid-summer; a blend between N186C and 187A.

*Stem surface.*—Glabrous.

*Branching habit.*—Basal and lateral branching; about 15 to 18 branches per basal branch, about 30 basal branches are produced per winter crown.

Foliage description:

*Leaf shape.*—Oblanceolate.

*Leaf division.*—Simple.

*Leaf arrangement.*—Whorled (sometime opposite).

*Leaf base.*—Truncate to cuneate.

*Leaf apex.*—Broadly acute-rounded.

*Leaf venation.*—Lower surface midrib; 144A to 144B suffused with 184A, upper surface midrib and lateral veins upper and lower surface; not conspicuous, color matched leaf color.

*Leaf margins.*—Entire and moderately serrulate.

*Leaf attachment.*—Sessile.

*Leaf orientation.*—Nearly horizontal to slightly upward, slightly cupped.

*Leaf texture.*—Thick, succulent.

*Leaf surface.*—Glandular and very slightly glaucous.

*Leaf color.*—Spring (and in summer when grown in shade) upper and lower surface; 137A, summer when grown in intense sunlight; blend between 137A and 139A and suffused with N79A, when in bloom in late summer and fall upper and lower surface; a blend between 137A and 139A and when suffused with N79A grown in intense sun.

*Leaf size.*—Average of 2.6 cm in length and 1.3 cm in width.

Flower description:

*Inflorescence type.*—Dense, slightly rounded cymes with an average of 3 terminal forked branches at terminus and upper lateral nodes, blooms are present on the top and sides of the plant.

*Inflorescence size.*—An average of 2.5 cm in diameter and 1.2 cm in depth (inclusive of forked branches) per individual cymes and up to 25 cm in length and 18 cm in width for the compound cyme.

*Lastingness of inflorescence.*—About one month.

*Flower type.*—Perfect, spreading, 5-starred.

*Flower number.*—An average of 20 flowers per branched cyme, about 40 flowers per stem.

*Flower fragrance.*—None.

*Flower buds.*—Ovate in shape, about 4 mm length and 2 mm in width, glabrous surface, a blend of 155C and 68A in color.

*Flower size.*—About 3 mm in depth and 6 mm in diameter.

*Peduncles.*—Round in shape, an average of 1.0 cm in length and 0.9 mm in width, secondary average 4.5 mm in length and 0.5 mm in width, 138B suffused with 184A in color, glabrous surface, peduncle leaves; an average of 3 per individual cyme, oblanceolate in shape, an average of 6 mm length and 2 mm in width, a blend between 137A and 139A, glandular and slightly glaucous on both surfaces.

*Pedicels.*—Round in shape, an average of 3 cm in length and 0.4 mm in width, 138B and lightly suffused with 184A in color, glabrous surface.

*Calyx.*—5-parted fused to tubular base, tips held nearly upright.

*Sepals.*—5, tube; about 1 mm in length and 2 mm in width, 138B in color, tips about 2 mm in length and 0.5 mm in width, lanceolate in shape, 138B in color on both surfaces, entire margin, narrowly acute apex, fused base, glaucous on both surfaces.

*Petals.*—5, spreading, 4 mm in length and 1.5 mm in width, lanceolate in shape, rounded base, acute apex, entire margin, color of inner and outer surfaces when opening; 155C and tinged with 68B, color when mature; N155D and suffused with 50C to 50D, becoming dry and upright and 155A and very lightly infused with 50D, glabrous on both surfaces.

Reproductive organs:

*Pistils.*—5, showy, held erect, about 2.1 mm in length 1 mm in width, stigma; 0.2 mm in width and 65D in color, style; 2 mm in length, 1 mm in width, ovate in shape and 65C in color, ovary; small, single celled and translucent in color.

*Stamens.*—10, about 1.5 mm in length, filament; very fine, 67A in color and 65D at base, anther; basified, about 0.5 mm in length and width, a blend of 202A and 8A in color, pollen is moderate in quantity and about 8A in color.

*Fruit.*—Fruit and seed production has not been observed to date.

It is claimed:

1. A new and distinct variety of *Sedum* plant named 'Jade Tuffet' as described and illustrated herein.

* * * * *